US00PP21943P2

(12) United States Plant Patent
Bathaeian

(10) Patent No.: US PP21,943 P2
(45) Date of Patent: May 31, 2011

(54) **VARIETY OF *VERBENA* PLANT NAMED 'SUMVERB 0901'**

(50) Latin Name: *Verbena hybridus*
Varietal Denomination: Sumverb 0901

(75) Inventor: Mehdi Bathaeian, Waltrop (DE)

(73) Assignee: Grünewald Veredelings B.V., 's Gravenzande (NL)

( * ) Notice: Subject to any disclaimer, the term of this patent is extended or adjusted under 35 U.S.C. 154(b) by 0 days.

(21) Appl. No.: 12/653,693

(22) Filed: Dec. 17, 2009

(51) Int. Cl.
*A01H 5/00* (2006.01)

(52) U.S. Cl. ..... Plt./308
(58) Field of Classification Search ..... Plt./308
See application file for complete search history.

(56) References Cited

OTHER PUBLICATIONS

UPOV ROM GTITM Computer Database, GTI Jouve Retrieval Software 2010/03 Citation for 'Sumverb0901'.*

* cited by examiner

*Primary Examiner* — Wendy Haas
(74) *Attorney, Agent, or Firm* — The Webb Law Firm

(57) ABSTRACT

A new and distinct *Verbena* plant named 'Sumverb 0901' having a compact growth habit and intense purple-colored flowers.

2 Drawing Sheets

Botanical classification: *Verbena hybridus.*
Varietal denomination: 'Sumverb 0901'.

BACKGROUND OF THE INVENTION

The present invention comprises a new and distinct cultivar of *Verbena* plant known by the varietal name 'Sumverb 0901'. The new variety was discovered in 2007 in a selected breeding program in Waltrop, Germany. The purpose of the breeding program was to produce a variety of *Verbena* with a new flower color. The new variety was selected from a cross of proprietary breeding plants identified as 1513 'Sumverb 13' (female parent, unpatented) and 04-829-2 (male parent, unpatented). The new variety exhibits similar foliage and compact growth habit to its parents, but exhibits a different flower color and size from both parents. Further, 'Sumverb 0901' has a similar compact growth habit to *Verbena* plant 'Temari Patio Blue' (unpatented), but 'Sumverb 0901' exhibits a more intense flower color than 'Temari Patio Blue', and the center of the flower of 'Temari Patio Blue' is not colored. The new variety was first asexually reproduced in June of 2007 by cuttings in Waltrop, Germany. The new variety has been trial and field tested and has been found to retain its distinctive characteristics and remain true to type through successive propagations.

The following traits also distinguish 'Sumverb 0901' as a new and distinct cultivar from other *Verbena* varieties known to the breeder:

1. Flower arrangement;
2. Growth habit;
3. Early flowering; and
4. Intense flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
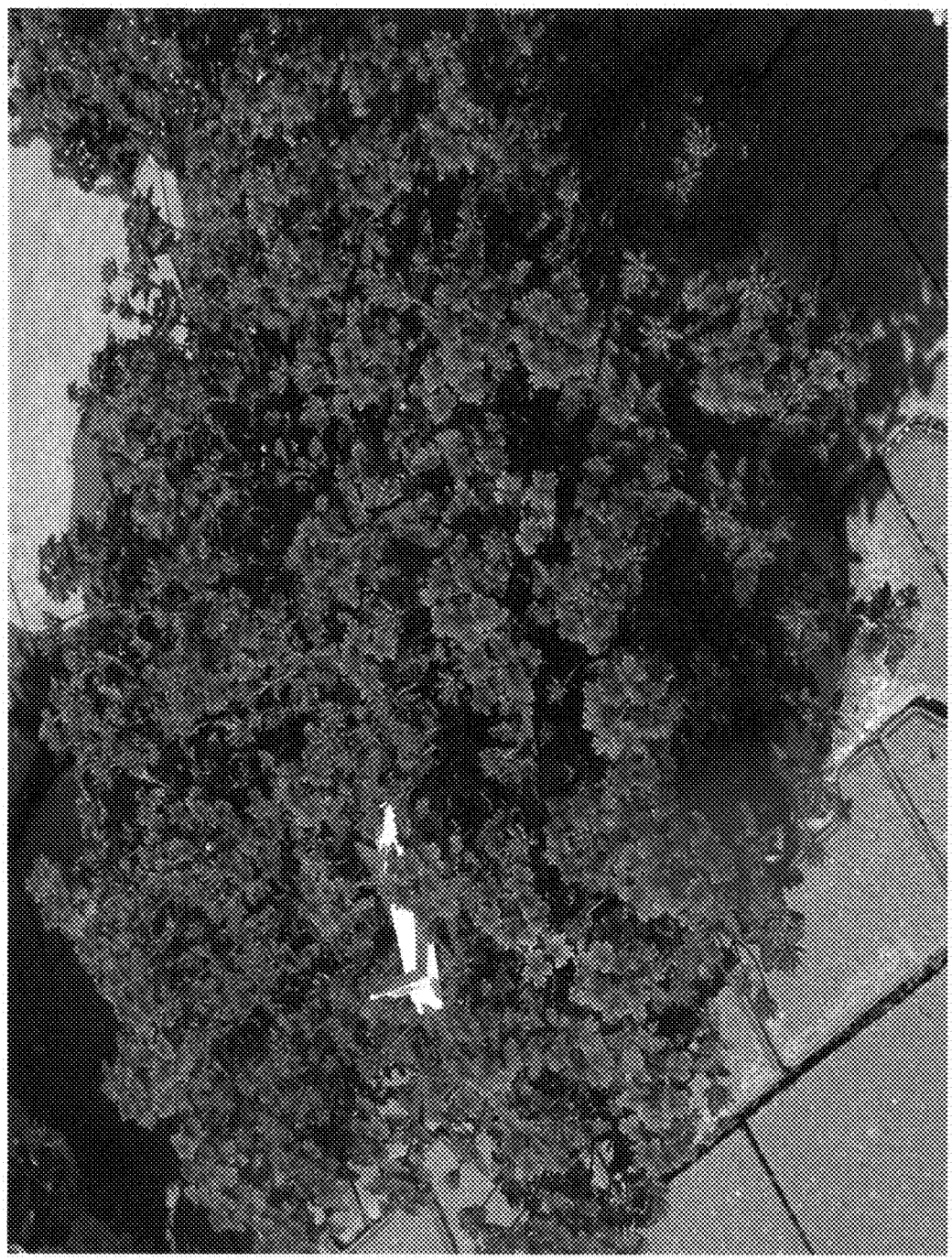
FIG. 1 is a photograph of the plant.
Figure 2:
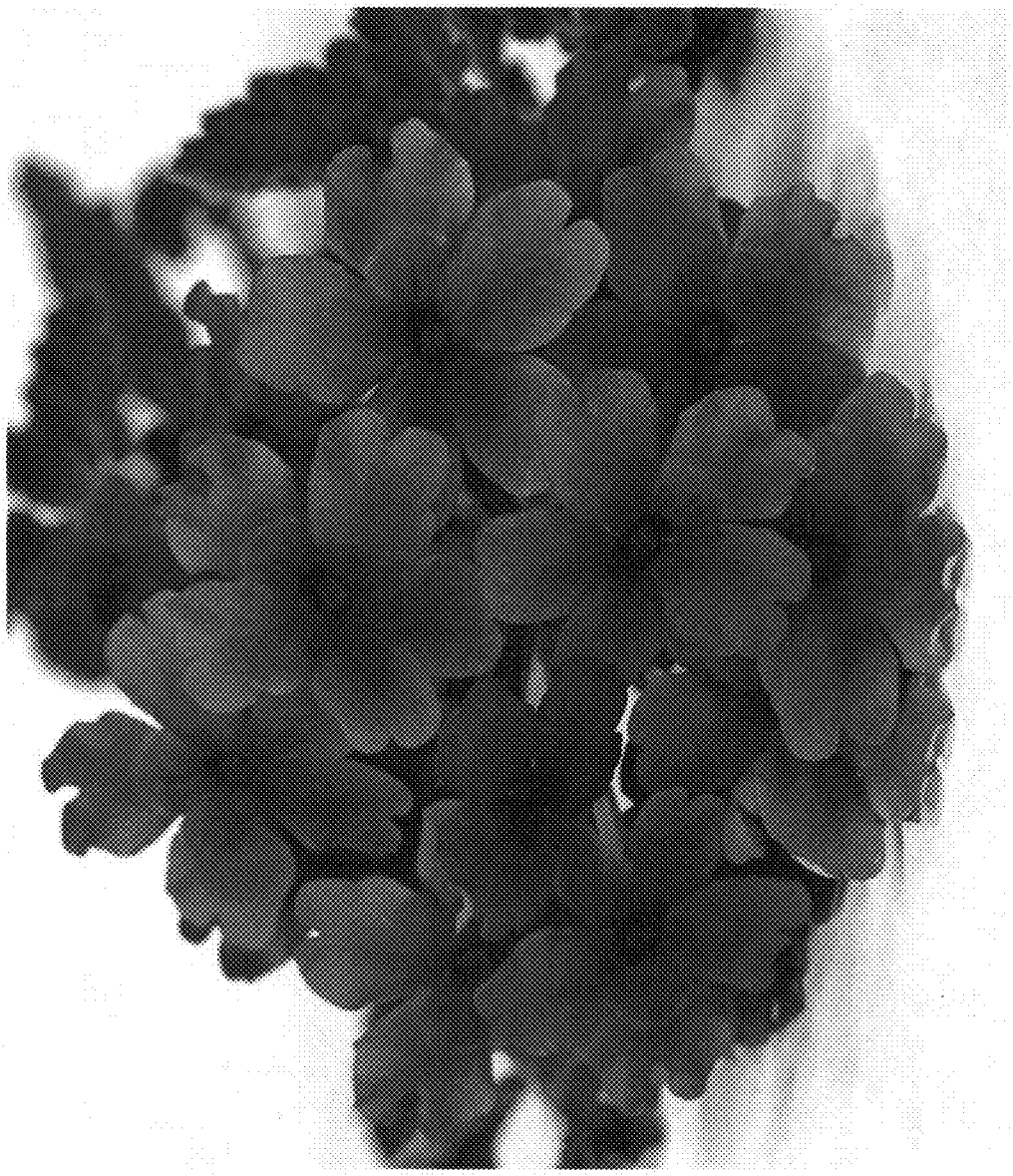
FIG. 2 is a close-up photograph of the flowers of the new variety.

The following detailed description sets forth characteristics of the new cultivar. The data which defines these characteristics were collected by asexual reproductions by cuttings carried out in Waltrop, Germany. Plants for the description were 7-8 weeks old from potting when described and grown under natural conditions in 11 cm pots. However, when grown in a hanging basket, a 30 cm basket is recommended. The color readings were taken under natural light. Color references are primarily to The 2001 R.H.S. Colour Chart of The Royal Horticultural Society of London.

PLANT

Height: 10-20 cm.
Diameter: 30 cm.
Vigor: Medium.
Roots:
- *Time to initiate roots.*—About 4 days at 18° C.
- *Time to develop roots.*—About 21 days at 18° C.

Time to finish a flowered plant: About 6 weeks in a 12 cm container.
Branching habit: Freely branching.
Lateral branches:
- *Length.*—15-20 cm.
- *Diameter.*—1-1.8 mm.
- *Color.*—144C.
- *Texture.*—Light pubescence present.
- *Internode length.*—20-25 mm.

Foliage:
- *Arrangement.*—Alternate.
- *Size of leaf.*—Length: 25-35 mm. Width: 12-19 mm.
- *Shape of leaf.*—Between lanceolate and elliptic.
- *Shape of apex.*—Subacute.
- *Shape of base.*—Cuneate.

*Aspect.*—Trulloid with margin.
*Margin.*—Serrated; jagged.
*Texture.*—Matte and veiny. Color: Young leaves: Upper surface: 137A. Lower surface: 137D. Mature leaves: Upper surface: 137A. Lower surface: 137C.
*Petiole.*—Length: 3-5 mm. Diameter: 1-1.5 mm. Color: 144B.
*Veins.*—Venation type: Spreaded. Color: Upper surface: 143B. Lower surface: 143C.

FLOWER

Start of flowering season: May in Germany.
Bud:
*Number.*—10-20 buds per bud stem.
*Shape.*—Linear.
*Diameter.*—2-3 mm.
*Length.*—11-13 mm.
*Color.*—137A.
Corymb:
*Number of flowers per corymb.*—10-20 total flowers and buds.
*Diameter.*—5-6 cm.
*Length.*—5-7 cm without the stem.
Corolla:
*Form.*—Actinomorphic.
*Petals/lobes.*—Number: 5. Length: 10-11 mm. Width: 6-7 mm. Shape: Heart-shaped; obcordate. Aspect: Heart-shaped. Margin: Undulate. Color: When opening and fully opened: Upper surface: 83B in the center with 80B edges. Lower surface: N81C.
*Throat.*—Texture: Smooth.
Calyx:
*Form.*—Narrowly oblong.
*Length.*—10-12 mm.
*Diameter.*—1-2 mm.
*Sepal.*—Shape: Narrowly oblong. Margin: Dentate. Texture: Soft pubescence. Color: Upper surface: 137A. Lower surface: 137B.
Disease resistance: No resistance to diseases noted to date.
Fragrance: None observed.
Temperature tolerance: Not tested.

REPRODUCTIVE ORGANS

Stamens:
*Number.*—Up to 4.
*Filament length.*—1-2 mm.
*Anthers.*—Shape: Ellipsoid to ovoid. Length: 0.8-1 mm. Color: 11B.
*Pollen.*—Color: 11A to 11B. Amount: Minimal.
Pistil:
*Length.*—3-4 mm.
*Style.*—Length: 7-8 mm. Color: 134C to 134D.
*Stigma.*—Shape: Almost rounded. Color: 134B.
Seed production: Self-pollination is low and other pollination is also low.

I claim:

1. A new and distinct variety of *Verbena* plant named 'Sumverb 0901' as shown and described herein.

* * * * *